United States Patent
Stora (12)

(10) Patent No.: US 6,403,109 B1
(45) Date of Patent: Jun. 11, 2002

(54) TRANSPARENT PERFUME COMPOSITION

(75) Inventor: Thierry Stora, Sergy (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 09/625,864

(22) Filed: Jul. 26, 2000

Related U.S. Application Data

(63) Continuation of application No. PCT/IB99/01948, filed on Dec. 6, 1999.

(30) Foreign Application Priority Data

Dec. 8, 1998 (CH) .............................................. 2437/98

(51) Int. Cl.$^7$ .......................... A61K 7/00; A61K 7/32; A61K 7/34; A61K 7/36; A61K 7/46

(52) U.S. Cl. .......................... 424/401; 424/65; 424/66; 424/67; 424/68; 512/1

(58) Field of Search .............................. 424/401, 65–68; 512/1

(56) References Cited

U.S. PATENT DOCUMENTS

| | | | | | |
|---|---|---|---|---|---|
| 4,803,195 | A | * | 2/1989 | Holzner | 512/4 |
| 4,948,578 | A | * | 8/1990 | Burger et al. | 424/68 |
| 5,216,033 | A | * | 6/1993 | Pereira et al. | 514/844 |
| 5,374,614 | A | * | 12/1994 | Behan et al. | 512/3 |
| 5,393,518 | A | * | 2/1995 | Kwass | 424/66 |
| 5,989,531 | A | * | 11/1999 | Schamper et al. | 424/65 |
| 6,007,799 | A | * | 12/1999 | Lee et al. | 424/65 |
| 6,033,651 | A | * | 3/2000 | Dolak et al. | 424/65 |
| 6,051,216 | A | * | 4/2000 | Barr et al. | 424/78.35 |
| 6,197,285 | B1 | * | 3/2001 | Kowalik et al. | 424/65 |

* cited by examiner

*Primary Examiner*—Jose' G. Dees
*Assistant Examiner*—Marina Lamm
(74) *Attorney, Agent, or Firm*—Winston & Strawn

(57) ABSTRACT

The invention concerns a transparent perfume composition substantially free of volatile organic solvents and in the form of an oil-in-water emulsion. The oil phase contains perfume ingredients, and the difference between the refractive indices of the oil phase and the aqueous phase is less than 0.003. This is achieved by adding agents with certain refractive indices to each of said phases.

20 Claims, No Drawings

TRANSPARENT PERFUME COMPOSITION

CROSS REFERENCE TO RELATED APPLICATION

This application is a continuation of the U.S. National Phase of International Application No. PCT/IB99/01948, filed Dec. 6, 1999, the content of which is expressly incorporated herein by reference thereto.

TECHNICAL FIELD

The present invention concerns the field of perfumery. It relates more particularly to a transparent perfume or cologne and essentially free of the volatile organic solvents current in parfumery.

PRIOR ART

In the preparation of perfumes and colognes the use of ethanol as a solvent is still very widespread. Ethanol makes it possible to solubilize well the perfuming ingredients used by the perfumers. Thus it is easy to incorporate each ingredient at the desired concentration and obtain a transparent solution. For this reason, most of the perfumes and colognes available on the market still contain ethanol, usually between 50 and 95% per volume.

Today consumers tend to prefer perfumes without alcohol or with a reduced content in alcohol, such that there is a requirement for replacing ethanol in the above-mentioned products.

It would be desirable to replace ethanol by water or an organic solvent which does not leave an important residue on the skin, or yet by a mixture of one or more of these solvents with water.

However in this context the use of water or a mixture of water with a non-volatile organic solvent leads to problems of solubility of the perfuming ingredients in the water phase because of their hydrophobic character. Although it is known that these hydrophobic ingredients can be emulsified in the oil-in-water (O/W) type emulsions, these formulations are not usually transparent.

Furthermore, transparent perfuming compositions are known from the prior art in the form of microemulsions containing important amounts of surfactants. In these microemulsions the perfume (oily phase) is dispersed in water in form of drops having a size of about 5–50 nm and thanks to the small size of the drops, the mixture, i.e. the microemulsion, is transparent. However, it is not desirable to need to incorporate an important amount of surfactants, relative to the amount of perfuming ingredients, as this limits considerably the amount of fragrance that can be incorporated in the mixture.

Another known transparent composition type is the nanoemulsion, characterised by an average size of the oily phase droplets below ca. 30–75 nm. The droplets are small enough to make the emulsion translucent or partially transparent. Although these emulsions present the advantage of needing lesser amounts of surfactants than the microemulsions, they present nevertheless the disadvantage that their process of preparation is often difficult and delicate. Such emulsions are for example the object of application EP 728 460. More precisely there is described in this document a transparent nanoemulsion of oily-in-water type obtained by addition of an amphiphillic, non-ionic and liquid lipid, at a temperature below 45° C. to obtain the desired emulsion. This lipid is used in a proportion of 2 to 10% by weight with respect to the total weight of the lipidic phase. As the oily phase, the patent application describes amongst others the use of natural and synthetic essential oils. The described emulsions are used in cosmetic compositions as a result of their capacity to penetrate the skin after topical application.

Finally, a "conventional" emulsion, in which the average size of the dispersed droplets is above 100 nm, is described in U.S. Pat. No. 5,798,111. The object of this patent is a highly viscous cosmetic emulsion, and more particularly a semi-solid transparent gel, comprising 10 to 97% by weight of an aqueous phase containing 2-methyl-1,3-propanediol and 2 to 90% by weight of an oily phase comprising silicon oil. These gels have an optic turbidity below 50 NTU at 21° C. In addition to the above-mentioned ingredients these cosmetic compositions may contain non-ionic surfactants. The compositions described in this document are too viscous to be used in perfume compositions such as perfumes or colognes.

DESCRIPTION OF THE INVENTION

The present invention aims at solving the various problems met in the prior art by providing perfuming composition devoid of volatile organic solvents or VOC defined by the E.P.A. (Environmental Protection Agency), in particular by providing an ethanol-free composition and which is transparent. As a perfuming composition it is meant here a composition with low viscosity in which one ore more perfuming ingredients are totally solubilized and which, unlike a cosmetic composition, is not meant to penetrate the skin upon application. The object of the present invention is thus a perfuming composition in the form of a oil-in-water (O/W) or water-in-oil (W/O) emulsion, the oil containing at least one perfuming ingredient, said emulsion containing from 5 to 50% by weight of a dispersed phase and from 95 to 50% by weight of a continuous phase, the difference between the refractive index n of the dispersed phase and the continuous phase being less than or equal to ca. 0.003, preferably less than or equal to ca. 0.001.

According to a preferred embodiment of the invention the viscosity of the perfuming composition is below 10 Pa.s, independently of the nature of the emulsion.

In the case of a O/W emulsion the continous phase is formed by the water (aqueous phase) and the dispersed phase is formed by the oil (oily phase). In the case of a W/O emulsion, also called inverse emulsion, the continuous phase is formed by the oil wherein the water is dispersed, thus forming the dispersed phase.

The perfuming ingredients are dissolved in the oily phase because of their hydrophobic character.

Following a preferred embodiment of the invention, the perfuming composition is formulated as a perfume or a cologne.

The perfuming compositions of the invention are obtained by addition to an emulsion of certain ingredients which act on both the oily and the aqueous phases.

The ingredients added to the perfuming compositions of the invention, and which are specified further on, have the effect of modifying the refractive index of the two phases, so as to form a transparent emulsion. We have in fact observed that the transparent emulsions of the invention can be obtained when the difference between the refractive index of the dispersed phase and that of the continuous phase does not exceed ca. 0.003. Preferably this difference is less than or equal to ca. 0.001.

The transparency of the emulsions of the invention is characterised by a transmission measured at 600 nm (cell of 1 cm thickness), typically higher than 60% and for many emulsions above 80%.

It is useful to note here that the refractive index of water is 1.33 and that the perfuming compositions typically used have a refractive index n generally comprised between 1.45 and 1.55. The addition of certain ingredients makes it possible to narrow the difference between the respective refractive indexes of the two phases so as to bring it within the limits defined above.

We have observed that in the context of this invention it is possible to use a certain number of substances or agents having the capacity of acting on both phases as desired and the choice of which depends on individual criteria that can be established for each composition. The above-mentioned agents shall thus be selected as a function of their compatibility with the nature of the perfume, their compatibility with the skin, the desired sensation of the transparent perfume after application on the skin and the chemical inertia of these agents vis-a-vis the perfuming ingredients. Furthermore, the substance which will be used to act on the aqueous phase must be soluble in this phase and the substance selected to act on the oily phase must of course be soluble in the oily phase.

It is therefore possible to use any substance which satisfies one or more of the important criteria for a given perfuming composition, provided that this agent is able to increase the refractive index n of the aqueous phase and to lower the refractive index n of the oily phase, such that the difference between the two refractive indexes is within the limits defined above (inferior or equal to 0.003).

The used substance may be a solid or a liquid.

When the agent is a liquid ingredient, there is used preferably a substance with a refractive index n higher than or equal to ca. 1.40, the most appropriate values of n being higher than or equal to ca. 1.43, in the case where said agent acts on the aqueous phase. In the case of a substance acting on the oily phase, its refractive index n shall preferably be lower than or equal to ca. 1.43, an index lower than or equal to ca. 1.40 being preferred.

If a solid substance is added to a perfuming composition of the invention, it is clear that it must be soluble in the oily or in the aqueous phase so as to lower, respectively increase, the refractive index of the phase on which it acts. In the context of the present invention, the choice of this solid substance will consequently be a function of its capacity to dissolve completely in the phase on which it acts and to thus adequately change the refractive index of this phase.

According to the present invention there is preferably used as the agent acting on the aqueous phase at least a compound selected amongst urea, a diol, a triol or a polyol of mono-, poly- or oligomeric nature or a derivative thereof. Examples of monomeric diols or triols include ethyleneglycol, 1,2-propanediol, 1,3-propanediol, 1,2-butanediol, 1,3-butanediol, 1,4-butanediol, 2,3-butanediol, 2-methyl-1,3-propanediol, 1,6-hexanediol, neopentylglycol, trimethylol-propane, and glycerol. Examples of oligomeric or polymeric diols, triols or polyols include diethyleneglycol, triethyleneglycol, dipropyleneglycol, polyethyleneglycols with varied chain lengths. Among the derivatives of the di-, tri- or polyfunctional alcohols, there can be mentioned as example the product commercialized under the name Lubrajel® (origin: United Guardian Inc., Hauppauge, N.Y., USA, distributed by Sederma, Le Perrey en Yvelines, France) containing glyceryl polymethacrylates stabilised with propyleneglycol.

As the agent acting on the oily phase, i.e. the phase that contains the perfuming ingredients of a given composition, it is preferred to use a volatile silicone fluid. By volatile silicone fluid it is understood here a fluid having a vapour pressure at room temperature, equal to or above that of ethanol. Non restrictive examples of silicone fluids that can be used in the present invention include linear or cyclic polydimethylsiloxanes having 2 to 10 silicon atoms, preferably from 4 to 6 silicon atoms, such as, for example, decamethyl tetrasiloxane, octamethylcyclotetrasiloxane, decamethylcyclopentasiloxane or dodecamethyl-cyclohexasiloxane, or any mixture of these compounds. Silicones of this type have CTFA designations such as dimethicone (in the case of linear siloxanes) and cyclomethicone (in the case of cyclic siloxanes). These fluids are commercialized by many companies, for example: Dow Corning: Fluids DC 244, 245, 246, 344 EU, 345 EU (mixture of cyclomethicones) or Fluid DC 200 (hexamethyldisiloxane); General Electric Silicones: SF 1173, 1202, 1204 (mixture of cyclomethicones), SF 1214 (mixture of cyclomethicones and dimethicones) or SF 96 (mixture of dimethicones); Wacker Silicones: Siloxane F 222, 223, 250, 251 (mixture of cyclomethicones), Siloxane F 221, Silicone Fluid SF 96, SWS 101 (mixture of dimethicones); Chemische Fabrik Th. Goldschmidt AG: Abil® K4, B 8839 (mixture of cyclomethicones), Abil® 10-10000 (mixture of dimethicones); Witco: L 7087 (dimethicone copolyol methylether), L 7607 (dimethicone copolyol).

The best results were obtained with Fluid DC 345 EU, which is a mixture composed of about 3 parts of decamethylcyclopentasiloxane, ca. 1 part of dodecamethyl-cyclohexasiloxane and small amounts of octamethylcy-clotetrasiloxane.

The silicones mentioned above, though volatile, are not part of the substances classified in the group of the volatile organic solvents (VOC according to the E.P.A.) and are thus advantageously used in the present invention.

Other substances added to the oily phase gave good results. Among others we can mention light paraffines, such as heptane, or isoparaffine fractions commercialized under the name of Isopar®, for example Isopar® C or Isopar® M of the company Esso.

Another class of substances that can be advantageously used according to the invention is the class of fluorinated and perfluorinated paraffines of oligometric and polymeric nature, which are of widespread use.

Of course it is also possible to add to the composition a small amount of lower alcohol such as ethanol or isopropanol, to the oily phase, i.e. to the perfume, or to use a perfume which is at least partially dissolved in a lower alcohol, which can also lead to a transparent emulsion as desired in the present invention. However, since these substances are classified as volatile organic solvents, their use is less advantageous.

The refractive index n of a finished perfuming composition according to the invention has a value between ca. 1.40 and 1.44.

The emulsions of the invention can contain from 5 to 50% by weight, preferably 10 to 35% by weight of dispersed phase and from 95 to 50% by weight, preferably 90 to 65% by weight of continuous phase. These values are relative to the total weight of the emulsion and are independent of the fact that the compositions of the invention are in the form of a W/O or a O/W emulsion.

The oily phase comprises 15 to 60%, preferably 20 to 50% by weight of perfuming ingredients.

20 to 65% of the aqueous phase is water.

The emulsions of the invention containing the above-specified ingredients can show a sufficient stability as such during stockage. It is in particular the case when one or more of the substances added with the aim of modifying the refractive index of the one or the other phase are able to stabilise the emulsion as a result of their surfactant properties.

If needed, there is still added to the composition of the invention, at least one surfactant to obtain a stable emulsion. This surfactant will be used in a proportion of 0 to 8%, preferably 0.1 to 5% by weight, relative to the total weight of the emulsion. The best results were obtained using 2 to 5% by weight of surfactant.

Different types of surfactants can be used in the context of the invention. One can mention non-ionic, cationic, anionic, the amphoteric surfactants and the phospholipids, which may all be used in the present invention. Preferably, there is used a non-ionic surfactant or a mixture of two non-ionic surfactants. As non-restrictive examples, the ethoxylated nonylphenol comprising 9 to 10 units of ethyleneglycol (on sale under the name of Triton® N-101; origin: Fluka, Switzerland) or the ethoxylated undecanol comprising 8 units of ethyleneglycol (on sale under the name of Imbentin® 0800; origin: Kolb AG, Switzerland) can be cited. Other examples include the surfactants known under the tradename Tween® (Origin: ICI, England), such as Tween® 20 [polyoxyethylene (20) sorbitan monolaurate], Tween® 40 [polyoxyethylene (20) sorbitan monopalmitate], Tween® 60 [polyoxyethylene (20) sorbitan monostearate] and Tween® 80 [polyoxyethylene (20) sorbitan monooleate], and the surfactants commercialized under the name of Span® (origin: ICI, England), such as Span® 20 (sorbitan monolaurate), Span® 40 (sorbitan monopalmitate), Span® 60 (sorbitan monostearate) and Span® 80 (sorbitan monooleate). One can further mention Cremophor® RH40 and RH60 (origin: BASF AG, Germany, which are ethoxylated hydrogenated ricin oils), Genapol® [origin: Hoechst AG, Germany, a sodium (alcohol polyglycol ether) laurylsulfate], the surfactant known under the name of Poloxamer® 407 (a diblock copolymer of ethylenoxyde and propylenoxyde, also commercialized under the names of Pluronic® F 127 and Pluracare® F 127, origin: BASF AG, Germany); Tetronic® (origin: BASF AG, Germany); DC 3225 C, DC 5200, DC 193 (origin: Dow Coming, USA); Abil® Em 97 (origin: Goldschmidt).

The perfuming ingredients that can be used in the present invention are all the ingredients commonly used in perfumery. These ingredients shall not be described in greater detail here, as their description cannot be exhaustive and the skilled person is able to chose using his general knowledge and as a function of the desired olfactory effect. These perfuming ingredients belong to a variety of chemical classes, as varied as alcohols, aldehydes, ketones, esters, ethers, acetates, nitrites, terpenic hydrocarbons, heterocyclic nitrogen- or sulfur-containing compounds, as well as essential oils of natural or synthetic origin. Many of these ingredients are furthermore described in reference textbooks such as the book of S. Arctander, Perfume and Flavour Chemicals, 1969, Montclair, N.J., USA, or its more recent versions, or other works of similar nature.

The emulsions of the invention can be easily prepared by conventional mixing and homogenising methods, which therefore do not require a more detailed description here.

According to the present invention, emulsions are created with an average drop size above 200 nm.

The invention will now be illustrated by the following non-restrictive examples, in which the temperatures are indicated in degrees Celsius, the proportions of the ingredients are given in % by weight and the abbreviations have the usual meaning in the art.

EMBODIMENTS OF THE INVENTION

EXAMPLES 1 and 2

Preparation of Transparent Perfuming Compositions in the Form of Oil in Water Emulsions The O/W-type emulsions containing perfuming bases have being prepared with the below-specified ingredients by current methods in the art.

EXAMPLE 1

| Ingredients | Parts by weight |
| --- | --- |
| Perfuming base * | 10.05 |
| Silicon DC ® 345 [1] | 24.93 |
| Perfluorodecaline | 2.23 |
| Water (pH 7) | 21.35 |
| 1,2-Butanediol | 36.43 |
| Tetronic ® 704 [2] | 2.50 |
| Abil ®0 Em 97 [3] | 2.50 |
| Total | 100.00 |

[1] origin: Dow Corning
[2] origin: BASF AG
[3] origin: Goldschmidt
* The perfuming base was obtained by mixing of the following ingredients:

| Ingredient | |
| --- | --- |
| Citronellyl acetate | 3 |
| Geranyl acetate | 9 |
| Linalyl acetate | 276 |
| 10% * Aldehyde C10 | 3 |
| 10% * Aldehyde C12 | 12 |
| Methyl anthranilate | 16 |
| Bergamot essential oil | 226 |
| Cetalox ® [1] | 5 |
| Lemon essential oil | 318 |
| Dihydromyrcenol [2] | 60 |
| Dipropyleneglycol | 20 |
| 10% * Elemi [3] | 20 |
| Fleuria 41063 B [4] | 3 |
| Ethyl linalol | 66 |
| 10% * 3-(4-Methoxyphenyl)-2-methylpropanal [4] | 30 |
| Geraniol | 6 |
| 50% * Habanolide ® [5] | 130 |
| Hedione ® [6] | 215 |
| Hedione ® HC [7] | 72 |
| 10% ** Indol | 12 |
| Iso E super [8] | 85 |
| Lavandin grosso essential oil | 26 |
| 1% Liffarome ® [9] | 20 |
| Linalol | 40 |
| Sfuma mandarin essential oil | 5 |
| 10% * Crinkled mint essential oil | 30 |
| Bigarade Neroli essential oil | 130 |
| Portugal Florida orange essential oil | 80 |
| Phenethylol | 9 |
| Petitgrain essential oil | 63 |
| Pipol | 5 |
| Rosemary essential oil | 16 |
| Terpineol | 9 |

-continued

| Ingredients | Parts by weight |
|---|---|
| Violet essential oil | 50 |
| 1% * Zestover [10] | 30 |
| Total | 2100 |

* in dipropyleneglycol (DIPG)
** in triethanolamine
1) 8,12-epoxy-13,14,15,16-tetranorlabdane
2) origin: International Flavours and Fragrances, U.S.A.
3) 5-allyl-1,2,3-trimethoxybenzene; origin: Calchauvet, Grasse, France
4) origin: Firmenich SA, Geneva, Switzerland
5) pentadecenolide; origin: Firmenich SA, Geneva, Switzerland
6) Methyl dihydrojasmonate; origin: Firmenich SA, Geneva, Switzerland
7) Methyl dihydrojasmonate with high content of isomer cis; origin: Firmenich SA, Geneva, Switzerland
8) 1-(octahydro-2,3,8,8-tetramethyl-2-naphtalenyl)-1-ethanone; origin: International Flavours and Fragrances, U.S.A.
9) 3-hexenyl methyl carbonate; origin: International Flavours and Fragrances, U.S.A.
10) 9-decen-1-ol; origin: International Flavours and Fragrances, U.S.A.

The refractive index of each of the two phases of the composition was measured at room temperature, once the aqueous and the oily phase had been put in contact and before addition of the surfactant. The refractive index n of the aqueous phase was 1.4098 and that of the oily phase was 1.4112, thus forming a transparent emulsion. The transmission of the emulsion, measured at a wave length of 600 nm in a 1 cm thickness cell, is 91.5%.

EXAMPLE 2

| Ingredients | Parts by weight |
|---|---|
| Perfuming base * | 10.29 |
| Silicon DC ® 345 [1] | 23.22 |
| Perfluorodecaline | 2.14 |
| Water (pH 7) | 22.29 |
| 1,2-Butanediol | 38.06 |
| DC 193 [2] | 2.00 |
| DC 3225C [2] | 2.00 |
| Total | 100.00 |

[1] See example 1
[2] Origin: Dow Corning
* The perfuming base was obtained by mixing the following ingredients:

| | |
|---|---|
| Benzyl acetate | 250 |
| Pipol acetate | 70 |
| Styrallyl acetate | 230 |
| Phenylacetic aldehyde | 10 |
| Ambrettolide ® [1] | 10 |
| Astrotone | 300 |
| Bergamot essential oil | 1160 |
| β-Ionone | 550 |
| Cassis essential oil | 150 |
| 50% * Cetalox ® [2] | 60 |
| Lemon essential oil | 850 |
| Citronellol | 210 |
| Damascenone | 20 |
| 4-Decanolide | 20 |
| Dihydromyrcenol [3] | 440 |
| Dipropyleneglycol | 20 |
| Ethyl linalol | 720 |
| 7-Methyl-2H,4H-1,5-benzodioxepin-3-one [4] | 100 |
| Floralozone ® [5] | 50 |
| 3-(4-Methoxyphenyl)-2-methylpropanal [4] | 170 |
| Fructone ® [6] | 100 |
| Galbex ® [4] | 50 |
| γ-Damascone | 5 |

-continued

| Ingredients | Parts by weight |
|---|---|
| Geranium essential oil | 30 |
| Grapefruit essential oil | 100 |
| Habanolide ® [7] | 1120 |
| Hedione ® [8] | 2890 |
| Hedione ® HC [9] | 950 |
| Heliopropanal [10] | 400 |
| Indol | 35 |
| Iso E Super [11] | 380 |
| Lavender grosso essential oil | 40 |
| Liffarome ® [12] | 1 |
| Lilial ® [13] | 1050 |
| Lyral ® [14] | 430 |
| Sfuma mandarin essential oil | 270 |
| Melonal [15] | 3 |
| Crinkled mint essential oil | 20 |
| Peony 434017 [4] | 60 |
| Peony white HS 100001 [4] | 200 |
| Phenethylol | 80 |
| Phenylhexanol | 50 |
| Pipol | 20 |
| Orange essential oil | 500 |
| Rosalva [16] | 4 |
| Benzyl salicylate | 400 |
| Pipol salicylate | 400 |
| 10% ** BHT [17] | 200 |
| Zestover [8] | 22 |
| Total | 15200 |

* in 2-(2-ethoxyethoxy)-1-ethanol
** in propyleneglycol
[1] origin: Givaudan-Roure SA, Vernier, Switzerland
[2] 8,12-epoxy-13,14,15,16-tetranorlabdane; origin: Firmenich SA, Geneva, Switzerland
[3] origin: International Flavours and Fragrances Inc., U.S.A.
[4] origin: Firmenich SA, Geneva, Switzerland
[5] 3-(4-ethylphenyl)-2,2-dimethylpropanal + 3-(2-ethylphenyl)-2,2-dimethylpropanal; origin: International Flavours and Fragrances Inc., U.S.A.
[6] 2-methyl-1,3-dioxalane-2-ethylacetate; origin: International Flavours and Fragrances Inc., U.S.A.
[7] pentadecenolide; origin: Firmenich SA, Geneva, Switzerland
[8] methyl dihydrojasmonate; origin: Firmenich SA, Geneva, Switzerland
[9] methyl dihydrojasmonate with high content of isomer cis; origin: Firmenich SA, Geneva, Switzerland
[10] 3-(1,3-benzodioxol-5-yl)-2-methylpropanal; origin: Firmenich SA, Geneva, Switzerland
[11] 1-(octahydro-2,3,8,8-tetramethyl-2-naphthalenyl)-1-ethanone; origin: International Flavours and Fragrances Inc., U.S.A.
[12] 3-hexenyl-methyl carbonate; origin: International Flavours and Fragrances Inc., U.S.A.
[13] 3-(4-tert-butylphenyl)-2-methylpropanal; origin: Givaudan-Roure SA, Vernier, Switzerland
[14] 4-(4-hydroxy-4-methylpentyl)-3-cyclohexene-1-carbaldehyde + 3-(4-hydroxy-4-methylpentyl)-3-cyclohexene-1-carbaldehyde; origin: International Flavours and Fragrances Inc., U.S.A.
[15] 2,6-dimethyl-5-heptanal; origin: Givaudan-Roure SA, Vernier, Switzerland
[16] 9-decen-1-ol; origin: International Flavours and Fragrances Inc., U.S.A.
[17] 2,6-di-tert-butyl-4-hydroxytoluene
[18] 2,4-dimethyl-3-cyclohexene-1-carbaldehyde; origin: Firmenich SA, Geneva, Switzerland The refractive index of each of the two phases of the composition was measured at room temperature, once the aqueous and the oily phase had been put in contact and before addition of the surfactant. The refractive index n of the aqueous phase was 1.4109 and that of the oily phase was 1.4132, thus providing a transparent emulsion. The transmission of the emulsion, measured at a wavelength of 600 nm in a 1 cm thickness cell, is 98.2%.

EXAMPLES 3 AND 4

Preparation of Transparent Perfuming Compositions in the Form of Water-in-oil Emulsions The W/O-type emulsions containing perfuming bases were prepared with the below-specified ingredients by current methods in the art.

EXAMPLE 3

| Ingredients | Parts by weight |
|---|---|
| Perfuming base * | 10.20 |
| Silicone DC ® 345 [1) | 55.12 |
| Perfluorodecaline | 4.17 |
| Water (pH 7) | 11.55 |
| 1,2-Butanediol | 6.96 |
| Abil ® EM 97 [2) | 2.00 |
| Total | 100.00 |

[1)] see example 1
[2)] origin: Goldschmidt
* see example 1

The refractive index of each of the two phases of the composition was measured at room temperature, once the aqueous and the oily phase had been put in contact and before addition of the surfactant. The refractive index n of the aqueous phase was 1.4050 and that of the oily phase was 1.4070, thus providing a transparent emulsion. The transmission of the emulsion, measured at a wavelength of 600 nm in a 1 cm thickness cell, is 65.4%.

EXAMPLE 4

| Ingredients | Parts by weight |
|---|---|
| Perfuming base * | 10.20 |
| Silicone DC ® 345 [1) | 55.12 |
| Perfluorodecaline | 4.17 |
| Water (pH 7) | 11.55 |
| 1,2-Butanediol | 16.96 |
| Abil ® EM 97 [2) | 2.00 |
| Total | 100.00 |

[1)] see example 1
[2)] see example 3
* see example 2

The refractive index of each of the two phases of the composition was measured at room temperature, once the aqueous and the oily phase had been put in contact and before addition of the surfactant. The refractive index n of the aqueous phase was 1.4075 and that of the oily phase was 1.4068, thus providing a transparent emulsion. The transmission of the emulsion, measured at a wavelength of 600 nm in a 1 cm thickness cell, is 58.8%.

By mixing the above-mentioned ingredients we obtained a stable perfuming composition in the form of an emulsion of the water-in-oil type.

What is claimed is:

1. Perfuming composition in the form of a oil-in-water or water-in-oil emulsion having an oil phase containing 15% to 60% by weight of one or more perfuming ingredients, said composition containing from 5 to 50% by weight of a dispersed phase and from 50 to 95% by weight of a continuous phase, with the difference between the refractive index n of the dispersed phase and the continuous phase being less than or equal to 0.003.

2. Perfuming composition according to claim 1, characterised in that the emulsion has a viscosity which is below than 10 Pa.s.

3. Perfuming composition according to claim 1, which further comprises a substance acting on the dispersed or continuous phase of the emulsion to change the refractive index of that phase.

4. Perfuming composition according to claim 3, characterised in that one phase is an oily phase and the other phase is an aqueous phase, wherein the substance acting on the oily phase is a liquid agent having a refractive index n of less than or equal to about 1.43 and the substance acting on the aqueous phase is a liquid agent having a refractive index n above or equal to about 1.40.

5. Perfuming composition according to claim 4, characterised in that the refractive index of the liquid substance acting on the oily phase is less than or equal to about 1.40 and the refractive index of the liquid substance acting on the aqueous phase is above or equal to about 1.43.

6. Perfuming composition according to claim 3, characterised in that the substance acting on the oily phase is a volatile silicone having a vapour pressure superior or equal to that of ethanol, a paraffin or a fluorinated or perfluorinated paraffin.

7. Perfuming composition according to claim 6, characterised in that the volatile silicone is a linear or cyclic polydimethylsiloxane having at least two silicon atoms.

8. Perfuming composition according to claim 6, characterised in that the volatile silicone is octamethylcyclotetrasiloxane, decamethylcyclopentasiloxane, or dodecamethylcyclohexasiloxane.

9. Perfuming composition according to claim 3, characterised in that the substance acting on the aqueous phase is urea or a diol, triol or polyol or a derivative thereof.

10. Perfuming composition according to claim 9, characterised in that the substance is ethylene glycol, 1,2-propanediol, 1,3-propanediol, 1,2-butanediol, 1,3-butanediol, 2,3-butanediol, 2-methyl-1,3-propanediol, 1,6-hexanediol, neopentyl glycol, trimethylolpropane, glycerol, diethyleneglycol, triethylene glycol, dipropylene glycol, a polyethylene glycol having a varied chain length or a glyceryl polymethacrylate.

11. Perfuming composition according to claim 9, characterised in that the diol is 1,2-butanediol.

12. Perfuming composition according to claim 1, further comprising a surfactant in an amount of up to 8% by weight.

13. Perfuming composition according to claim 12, characterised in that the surfactant is present in an amount of 0.1 to 5% by weight.

14. Perfuming composition according to claim 12, characterised in that the surfactant is non-ionic.

15. Perfuming composition according to claim 1, in the form of a perfume or a cologne.

16. Perfuming composition according to claim 1, characterised in that the difference between the refractive index n of the dispersed phase and the continuous phase is less than or equal to 0.001.

17. Perfuming composition in the form of a transparent oil-in-water emulsion having a viscosity which is below than 10 Pa.s and comprising: 5 to 50% by weight of a dispersed oily phase containing 15% to 60% by weight of one or more perfuming ingredients, and from 50 to 95% by weight of a continuous aqueous phase, with the difference between the refractive index n of the dispersed phase and the continuous phase being less than or equal to 0.003.

18. Perfuming composition according to claim 17, which further comprises a liquid agent having a refractive index n of less than or equal to about 1.43 acting on the oily phase of the emulsion to change the refractive index of that phase, and a liquid agent having a refractive index n above or equal to about 1.40 acting on the aqueous phase of the emulsion to change the refractive index of that phase.

19. Perfuming composition in the form of a transparent water-in-oil emulsion having a viscosity which is below than 10 Pa.s and comprising: 5 to 50% by weight of a dispersed aqueous phase containing 15% to 60% by weight of one or more perfuming ingredients, and from 50 to 95% by weight of a continuous oily phase, with the difference between the refractive index n of the dispersed phase and the continuous phase being less than or equal to 0.003.

20. Perfuming composition according to claim 19, which further comprises a liquid agent having a refractive index n of less than or equal to about 1.43 acting on the oily phase of the emulsion to change the refractive index of that phase, and a liquid agent having a refractive index n above or equal to about 1.40 acting on the aqueous phase of the emulsion to change the refractive index of that phase.

* * * * *

UNITED STATES PATENT AND TRADEMARK OFFICE
CERTIFICATE OF CORRECTION

PATENT NO.    : 6,403,109 B1
DATED         : June 11, 2002
INVENTOR(S)   : Stora It is certified that error appears in the above-identified patent and that said Letters Patent is hereby corrected as shown below:

<u>Title page,</u>
Item [56], References Cited, U.S. PATENT DOCUMENTS, please insert:
-- 5,456,906    10/1995    Powell et al. ............ 424/66
5,534,246    7/1996    Herb et al. .............. 424/66
5,753,241    5/1998    Ribier et al. ............ 424/401
5,798,111    8/1998    Kanga et al. ............ 424/401 --

-- FOREIGN PATENT DOCUMENTS
        EP    0 728 460    8/1996
        FR    2 618 351    1/1989
        JP    11018709     1/1999
        GB    2 283 914    5/1995 --

Signed and Sealed this

First Day of October, 2002

*Attest:*

*Attesting Officer*

JAMES E. ROGAN
*Director of the United States Patent and Trademark Office*